United States Patent [19]

Layne

[11] Patent Number: 6,096,027
[45] Date of Patent: Aug. 1, 2000

[54] BAG ENCLOSED STENT LOADING APPARATUS

[75] Inventor: Richard Layne, Phoenix, Ariz.

[73] Assignee: Impra, Inc., a subsidiary of C.R. Bard, Inc., Tempe, Ariz.

[21] Appl. No.: 09/310,763

[22] Filed: May 12, 1999

Related U.S. Application Data

[60] Provisional application No. 60/102,404, Sep. 30, 1998.

[51] Int. Cl.[7] .................................................... A61B 17/00
[52] U.S. Cl. .............................. 606/1; 606/108; 606/198
[58] Field of Search ............................... 606/1, 108, 106, 606/109, 192, 194, 195, 198, 200, 209; 623/1, 12

[56] References Cited

U.S. PATENT DOCUMENTS

| | | |
|---|---|---|
| 3,540,431 | 11/1970 | Mobin-Uddin . |
| 4,740,207 | 4/1988 | Kreamer ........................................ 623/1 |
| 4,943,297 | 7/1990 | Saveliev et al. . |
| 5,382,260 | 1/1995 | Dormandy, Jr. et al. . |
| 5,591,222 | 1/1997 | Susawa et al. ................................ 623/1 |
| 5,626,604 | 5/1997 | Cottone, Jr. . |
| 5,630,830 | 5/1997 | Verbeek . |
| 5,649,950 | 7/1997 | Bourne et al. . |
| 5,672,169 | 9/1997 | Verbeek . |
| 5,676,671 | 10/1997 | Inoue . |
| 5,683,451 | 11/1997 | Lenker et al. . |
| 5,693,066 | 12/1997 | Rupp et al. . |
| 5,693,089 | 12/1997 | Inoue ............................................ 623/1 |
| 5,725,519 | 3/1998 | Penner et al. ................................. 606/1 |
| 5,733,325 | 3/1998 | Robinson et al. ............................. 623/1 |
| 5,738,674 | 4/1998 | Williams et al. . |
| 5,749,921 | 5/1998 | Lenker et al. ................................ 623/1 |
| 5,800,517 | 9/1998 | Anderson et al. ............................ 623/1 |
| 5,810,873 | 9/1998 | Morales ..................................... 606/198 |

FOREIGN PATENT DOCUMENTS

WO 98/20812  5/1998  WIPO .

*Primary Examiner*—Jeffrey A. Smith
*Assistant Examiner*—Eduardo C. Robert
*Attorney, Agent, or Firm*—Graham & James LLP

[57] ABSTRACT

An apparatus for loading a stent onto or into a catheter. A flexible sterile sleeve is provided to encase the stent as it is pulled through a loading device. The loading device is a simple design utilizing a tapered passageway. The passageway has first diameter at a proximal end which tapers to a second diameter, forming a funnel. The passageway continues at the second diameter forming a tube. The sleeved stent is pulled through the loading device from the proximal end to the distal end, smoothly compressing the stent. Depending on the type of stent and catheter being used, the stent is either crimped onto the catheter as it is pulled through the funnel, or is loaded into a catheter positioned at the distal end of the loading device. The sleeve acts to minimize the frictional forces to which the stent is subjected and to eliminate the longitudinal force that the stent would be subjected to if pushed or pulled directly. The sleeve may be close-ended to provide an additional sterility barrier about the stent.

15 Claims, 4 Drawing Sheets

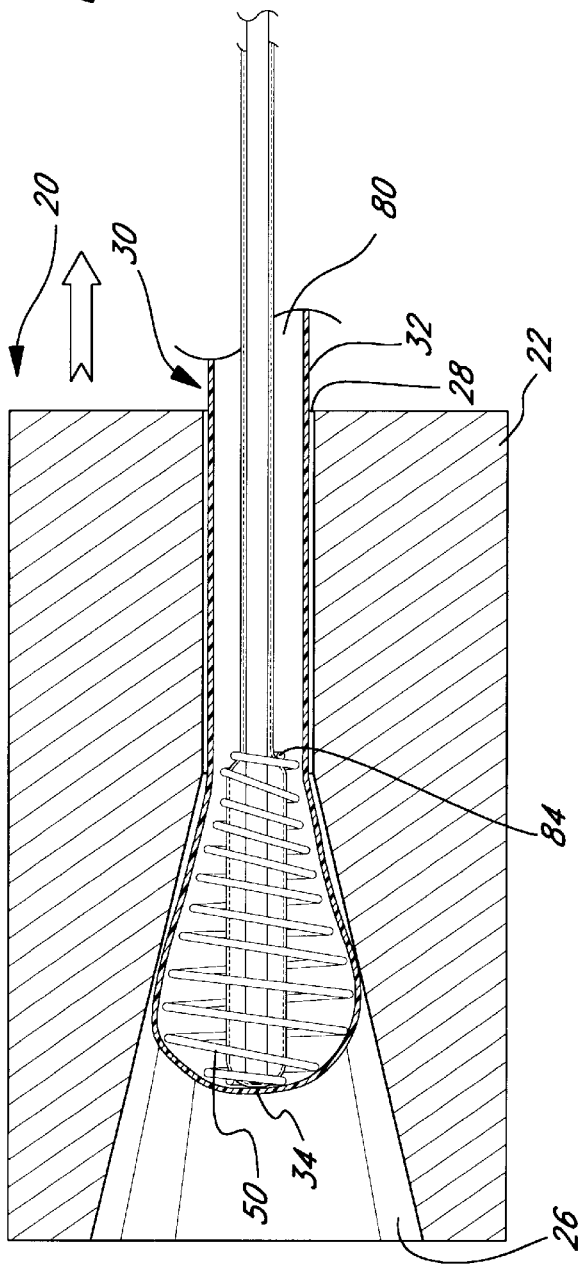
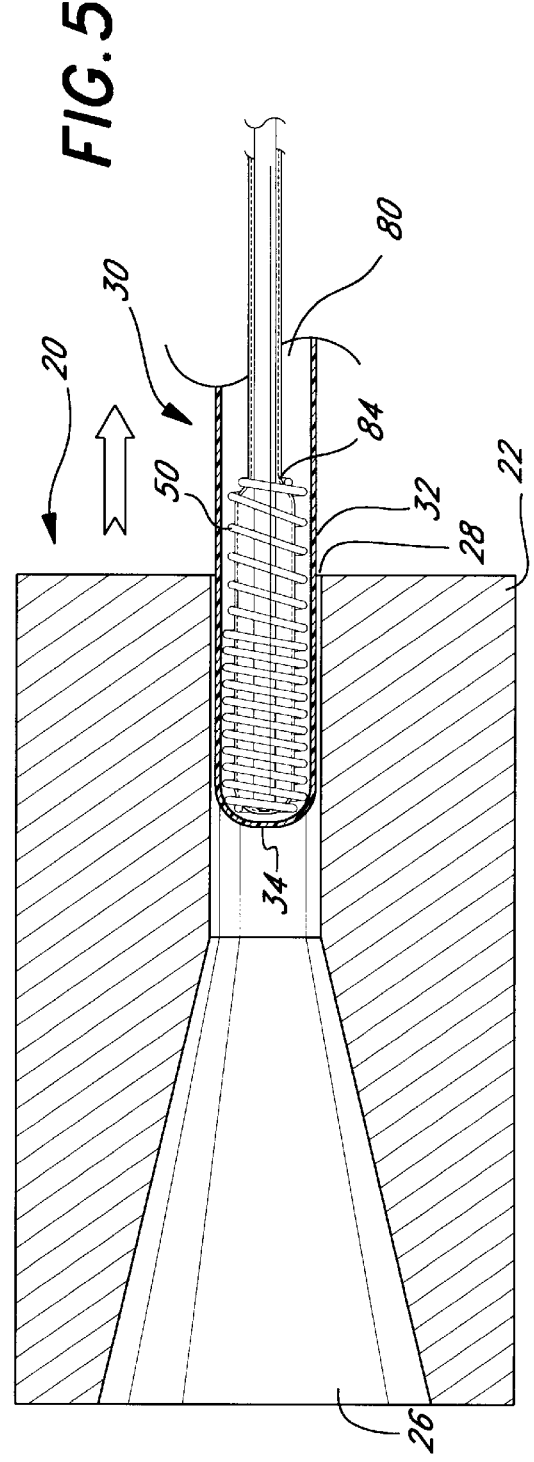

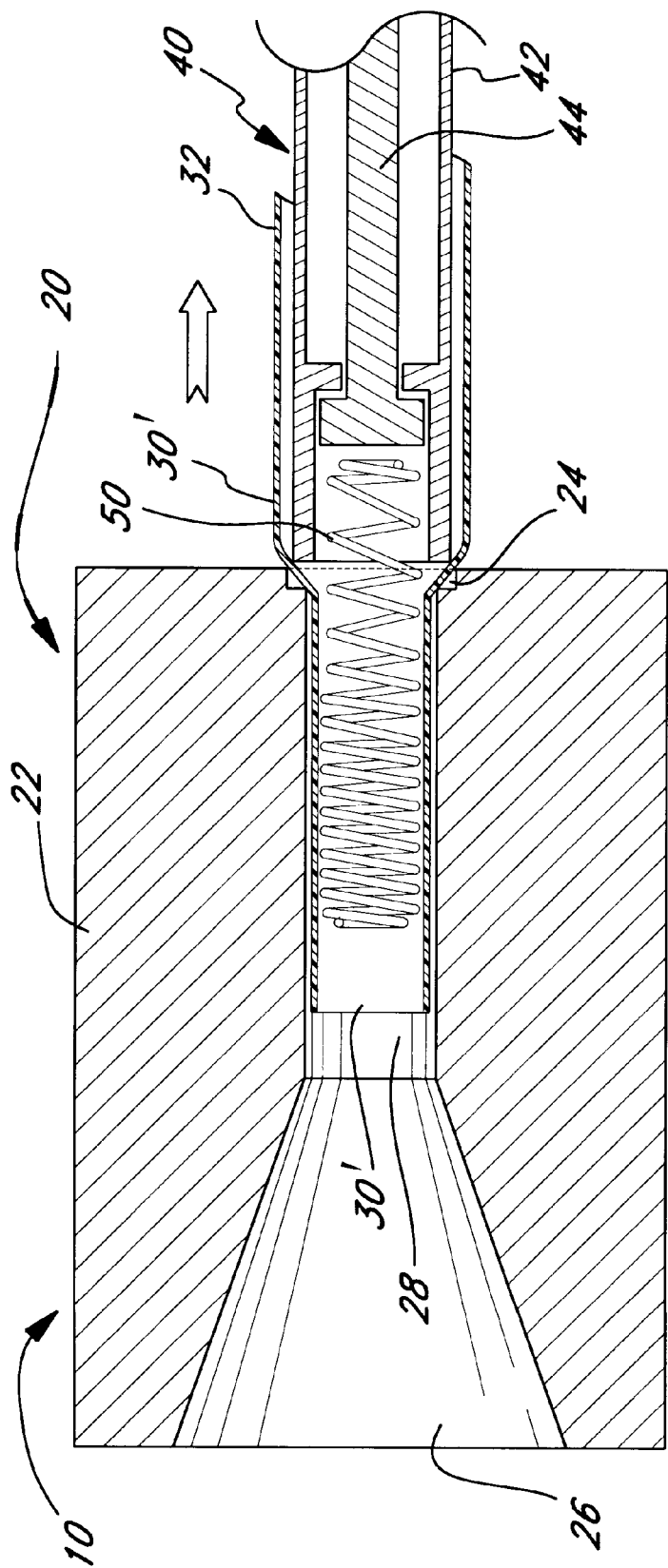

BAG ENCLOSED STENT LOADING APPARATUS

The present application is a continuation-in-part of U.S. Provisional Application No. 60/102,404 filed on Sep. 30, 1998. Priority is claimed from that application which application is incorporated herein by reference.

BACKGROUND OF THE INVENTION

1. Field of the Invention

The present invention relates generally to the field of medical devices, and more particularly, to devices for loading stents onto or into a catheter for use in a medical procedure.

2. Description of Related Art

Stents and similar endoluminal devices are currently used by medical practitioners to treat vessels that become narrowed so that flow through the vessels is restricted. This problem arises, for example, as a result of the disease process known as arteriosclerosis or after an angioplasty of a coronary artery to correct arteriosclerosis when excess tissue proliferation blocks the newly opened vessel. Stents can also be used to reinforce collapsed or narrowed tubular structures in the respiratory system, the reproductive system, biliary ducts or any other tubular body lumen. A procedure for inserting stents often involves first passing a guide wire through the affected area of the lumen. A catheter is then inserted over the guide wire and advanced to the site. The stent is inserted either simultaneously with the catheter (e.g., is present on the tip of the catheter) or immediately following insertion of the catheter (e.g., is passed through the catheter).

In many cases, an angioplasty balloon catheter will be advanced to the affected site. The balloon is then inflated, compressing the growth or material causing the narrowing. A stent is then inserted into the compressed area to prevent restenosis of the vessel. In some cases a balloon catheter with a metal stent crimped over the balloon is used. This device is inserted into the affected site and the balloon inflated, thereby enlarging the stent to its full size and compressing the growth. Still another variation is placing a compressed self-expanding stent inside a catheter. After the catheter is advanced to the affected site, the stent is released from the catheter, whereupon it expands to its full size.

Whichever method is used, the stent must first be "loaded" onto or into the delivery catheter. One common way of accomplishing this is for the physician to hand crimp the stent over the end of a balloon catheter. The physician selects the appropriate size and type of stent and manually deforms it with his or her fingers to crimp it over the balloon prior to insertion of the balloon catheter into the patient. This procedure is not optimal because there is a lack of uniformity in the crimping process. The stent may either be inadequately compressed or be excessively compressed so that it is mechanically damaged. In addition, traditional loading methods potentially subject the stent to contamination.

Many prior art solutions to the problems of stent compression have involved the use of tapering passageways or "funnels". The stent is inserted into the funnel in an enlarged state and is pulled or pushed through the funnel, compressing the stent onto a balloon catheter which has been inserted inside the small end of the funnel. U.S. Pat. No. 5,693,089 to Inoue discloses one such device. In this reference, a stent is crimped onto a balloon catheter by pulling the stent through the funnel. The disadvantage to this approach is that pushing or pulling a sometimes fragile stent onto a delivery device will distort and/or permanently damage the stent. Another example is shown in U.S. Pat. No. 5,725,519 to Penner et al. which discloses loading a stent onto a balloon catheter by means of a two piece device which employs a funnel-shaped bore to compress the stent. The Penner et al. device incorporates an open-ended flexible tube to surround the stent. While Penner addresses the need for uniformity in compressing stents, it is intended to crimp stents onto balloon catheters and cannot be used to load stents into catheters. Further, it does not contemplate an embodiment to completely enclose and protect the sterility of a stent. Therefore, it is desirable to provide a loading device for stents that would uniformly compress or crimp a stent onto or into a catheter while minimizing manipulation of the stent prior to the crimping process.

SUMMARY OF THE INVENTION

The present invention compresses and loads stents onto or into a catheter by using either an open-ended sleeve to prevent stress to the stent or a closed-end bag prevent stress and preserve sterilely.

It is an object of this invention to minimize the frictional (shear) forces acting on the wall of a stent during the process of loading a stent onto or into a catheter.

It is a further object of the present invention to provide a procedure for crimping a stent onto or into a catheter while maintaining stent sterility.

These and additional objects are accomplished using either an open-ended sleeve or a close-ended sleeve ("bag") and a loading device. First, a full-sized stent is placed into a flexible sleeve (either open or close-ended). This step is contemplated to be carried out by the manufacturer. The enclosed stent would be inserted into sterile packaging and subjected to routine sterilization procedures (e.g., radiation or chemical sterilization). Alternatively, sterile sleeves can be provided for "field loading" of the stent. The sleeve or bag can consist of many different materials, such as polyethylene, polytetrafluoroethylene ("PTFE") or especially expanded polytetrafluoroethylene ("ePTFE"). The bag may be advantageously treated with various coatings to lubricate passage of the stent through the funnel. In the case of an open-ended sleeve, the inner surface is advantageously coated with a biocompatible "tacky" coating to enhance friction between the sleeve and the stent. Typically, the sleeve or bag is longer than the stent so that the end of the bag or sleeve can be threaded through the small orifice of the loading device and grasped. The catheter to be loaded is then placed into the loading device so that the distal end of the catheter lies near the proximal (small) orifice of the funnel-shaped loading device. The sterile outer packaging material is opened, and the bag with the stent inside is then inserted over the catheter end and the bag and stent are simultaneously pulled through the loading device from large orifice to small orifice. This results in a catheter with a stent uniformly compressed onto its end and with the bag over the end to maintain sterile conditions. Although the loading procedure normally takes place in a sterile operating environment, the sleeve provides an additional barrier to guarantee stent sterility. Even an open ended sleeve provided significant protection against contamination. Because the stent is left in the patient indefinitely, even a single pathogenic organism might cause serious complications. Immediately before the stent is inserted into the patient, the bag can be removed. Removal of the bag or sleeve can consist of sliding it back off of the device, or tearing it off using a tear strip (e.g., an embedded length of fiber that can be pulled to cut open the sheath). Also, tear away seams or perforations can be incorporated into the bag or sleeve for easy removal.

Providing a buffer layer of sleeve material over the stent is beneficial in at least two ways. First, the layer acts to minimize the frictional forces to which the stent is subjected in being reduced it from full diameter. Second, by pulling the bag or sleeve rather than directly pushing or pulling the stent, the longitudinally applied force is avoided, thereby reducing stresses to the stent. As a result there is less chance of perforating any covering (e.g., an encapsulated stent) or of damaging the stent struts through bending or fracture.

The loading device consists of a block of material traversed by a passageway of varying diameter (e.g., funnel-shaped). At the proximal end of the block, the passageway has its widest first diameter. This wide first diameter tapers down to a second smaller diameter, thereby forming a funnel shape. The second diameter runs throughout the remainder of the block forming a tubular shape. The cross-section of the second diameter can be circular or can be other shapes such as a rounded star (e.g., a star shape wherein the arms have rounded tips) to aid in the compression and folding of the bag and/or enclosed stent. The funnel-shaped passageway can be produced by drilling or cutting a solid block of material (plastic such as an acrylic or metal such as aluminum). The passageway can also be produced by well-known methods of molding. Alternatively, the funnel-shape can be constructed from formed sheet metal, etc.

This device is useful not only for loading a stent onto a catheter, as described above, but can also be used to load a stent into a catheter. In this case, the catheter is placed into a port at the distal end of the loading device. This port has a diameter larger than the second diameter and is large enough to accommodate a catheter designed for loading stents inside. The bagged stent is then pulled through the device and into the catheter. The bag or sleeve is pulled over the catheter at the same time and remains in place until the catheter is used on a patient. The bag or sleeve can be sealed (closed) at the distal end at least. If the sleeve is to be pulled over the catheter (rather like putting on a sock) as described above, then the proximal end, at least, must be left open. Although the sleeve may be open at both ends, it is advantageous to enclose the stent by sealing both ends to allow for the stent to be sterilized. Then one end can be sterilely opened just before compression of the stent. Alternatively, the bag can be split to pass over and around the end of the catheter. If the sleeve is to be pulled through the catheter, it is not necessary to even have even a single open end, and the bag can remain completely closed to ensure sterility.

BRIEF DESCRIPTION OF THE DRAWINGS

FIG. 4 is a longitudinal-sectional view of an embodiment of the stent loading apparatus in the initial phases of compressing a stent onto an angioplasty balloon.

FIG. 5 shows the device of FIG. 4 after completion of the stent compression.

FIG. 7 is a longitudinal-sectional view of the embodiment of FIG. 1 used with an open-ended sleeve.

DETAILED DESCRIPTION OF THE PREFERRED EMBODIMENT

Figure 1:
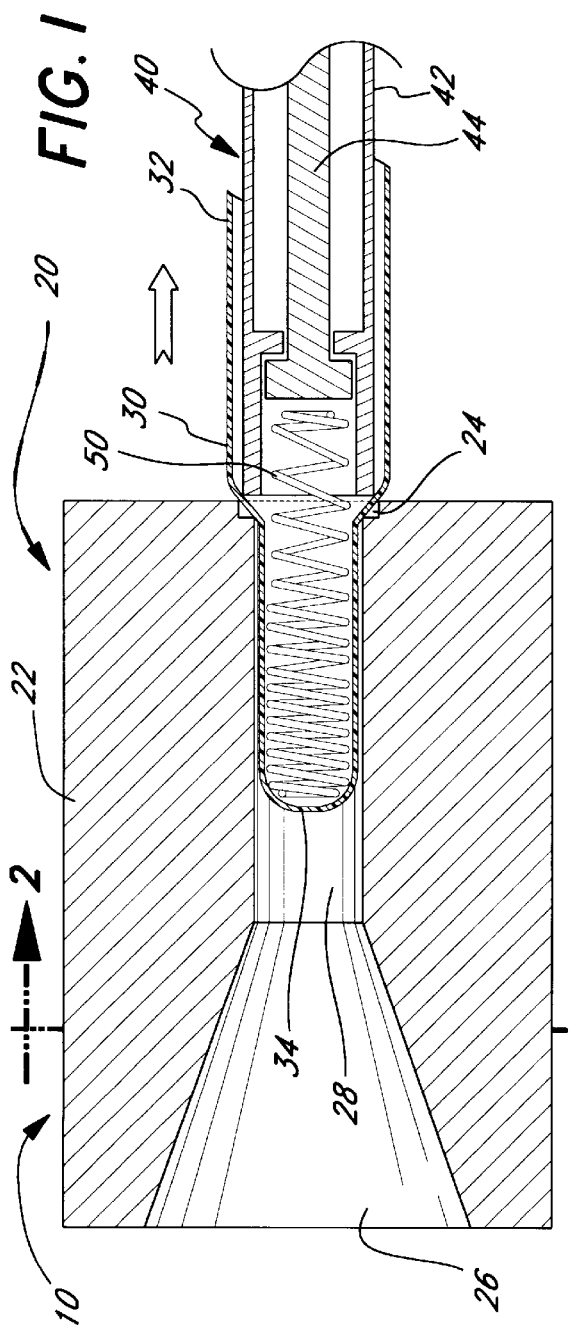
FIG. 1 is a longitudinal-sectional view of a first embodiment of a stent loading apparatus.

Referring now to the drawings, in which like reference numbers represent similar or identical structures throughout, FIG. 1 depicts a stent loading apparatus 10 consisting of a loading device 20 and a closed ended sleeve 30 (this and all other embodiments can be used with an open-ended sleeve as well). A stent 50 and a catheter 40 in which the stent 50 is loaded are also shown. The loading device 20 is a block 22 which has at its center a passageway of varying diameter. This passageway can be coated with PTFE or other low friction material that facilitates the movement of the bag-enclosed stent 50. At the proximal end of the block 22, the passageway has its largest diameter 26. From there the passageway tapers to a second diameter 28 thus forming a funnel shape. The second diameter 28 is constant to the distal end of the block, forming a tube.

Figure 2:
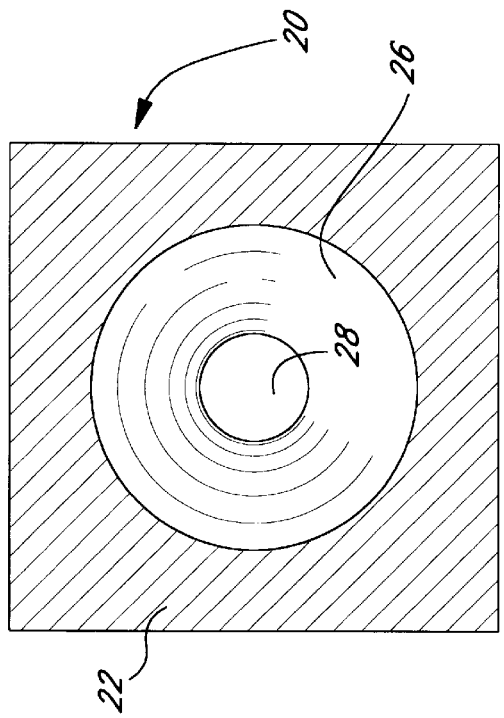
FIG. 2 is a cross-sectional view of FIG. 1 taken at 2—2.

FIG. 2 shows a cross-section of the loading device 20. At the distal end of the block 22, the tube-like section of the passageway widens to a third diameter 24 to permit the docking of a catheter 40. Pulling the stent 50 through the loading device 20 compresses it from its full diameter to the illustrated smaller diameter. To accomplish this the stent 50 is placed inside of the sleeve 30 prior to being pulled through the passageway. As mentioned above, there are advantages to using a sleeve 30 which is initially closed at both ends. In such a case one end is opened prior to the compression process leaving only a single closed end 34. The sleeve 30 is pulled through the loading device 20 by extensions 32 of sleeve material located near the open end. As the sleeve 30 is pulled through the loading device 20, compressing the stent, it is also pulled over the end of the catheter 40. The sleeve 30 is pulled until the stent 50 is entirely inside the catheter 40, where it comes in contact with a catheter unloading arm or plunger 44. Following loading the sleeve 30 can remain over the end of the catheter 40 with its closed end 34 sealing the stent 50 from the outside. Of course, the bag 30 must be torn off prior to insertion of the catheter into the patient.

The sleeve 30 can be made from any of a number of plastic films such as polyethylene, polyvinyl, polyurethane, cellulose, and PTFE. PTFE is especially preferred because it is "slippery". Alternately, other plastic films can be coated with antifriction materials. It may also be advantageous to coat the inside surface with a slightly plastic or tacky composition to "grip" the stent and control the movement of the film relative to the stent so that forces are uniformly applied to the length of the stent 30 as opposed to being applied just by the end 34 of the bag. With an open-ended sleeve as shown in FIG. 7 such a "gripping" coating is especially important. Expanded PTFE is especially preferred because this material is readily permeable to air. Thus, a sleeve that is closed at both ends can be readily compressed since the air easily escapes through the ePTFE. If a closed sleeve of other plastic films is used, special provision must be made for escape of trapped air during the compression process.

In the case of stents fabricated from shape memory alloy the passageway can advantageously be fabricated from a metal with circulation channels for refrigerant embedded in the walls of the passageway. The stent is thereby chilled below its transformation temperature as it is pulled through the device. In this case the stent may advantageously be pulled fairly slowly to allow complete temperature equilibration.

Figure 3:
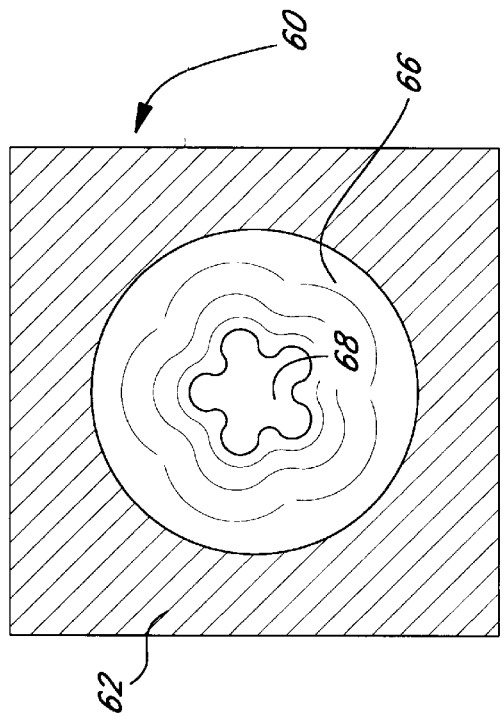
FIG. 3 is a cross-sectional view of an alternative embodiment of the stent loading device (also taken at a point corresponding to 2—2).

There are many different possibilities for the cross-sectional shape of the passageway of the loading device 20. FIG. 3 depicts a cross-section of a second embodiment of the invention, showing a loading device 60, with a block 62, a first diameter 66 and a second diameter 68. In this embodiment, however, the second diameter 68 is not round and is instead a rounded "star" shape. This design illustrates an additional way to crimp the stent 50 onto or into a catheter as the cross-sectional shape of the passageway promotes folding of the sleeve 30 and/or of the stent 50, itself. It is specifically contemplated that the number of lobes of the cross-section be related to the underlying structure of the stent so that folding and crimping is induced in the most favorable areas of the stent or encapsulated stent.

FIG. 4 shows a third embodiment of the present invention comprising the loading device 20, the sleeve 30, and the stent 50. This embodiment is different, however, in that the catheter 80 is a balloon catheter. The balloon tip of the catheter 80 is inserted inside of the tube created by the second diameter 28 until the distal end of the catheter 80, bearing by a deflated balloon 84, is near the first diameter 26 of the loading device 20. In FIG. 4, the stent 50 is shown in the process of being compressed. The sleeve 30 is pulled through the loading device 20 so that the stent 50 begins to compress around the balloon 84. At this point the end 34 of the sleeve 30 reaches the distal tip of the catheter 80 and both the stent 50 and the catheter 80 are pulled through the passageway so that the stent 50 is securely crimped around the balloon portion 84 of the catheter 80 as shown in FIG. 5. Again, the end result is the sterile catheter 80 with the stent 50 loaded onto it, encased in the bag-sleeve 30. Again, the bag 30 is removed before the catheter 80 is used on a patient. As discussed above, the sleeve 30 can be removed in a variety of ways including pulling a pre-designed tear strip. The sheath 30 can be removed prior to catheter insertion; alternatively, it can be composed of a polymer that spontaneously dissolves in the aqueous milieu of the patient's blood stream.

Figure 6:
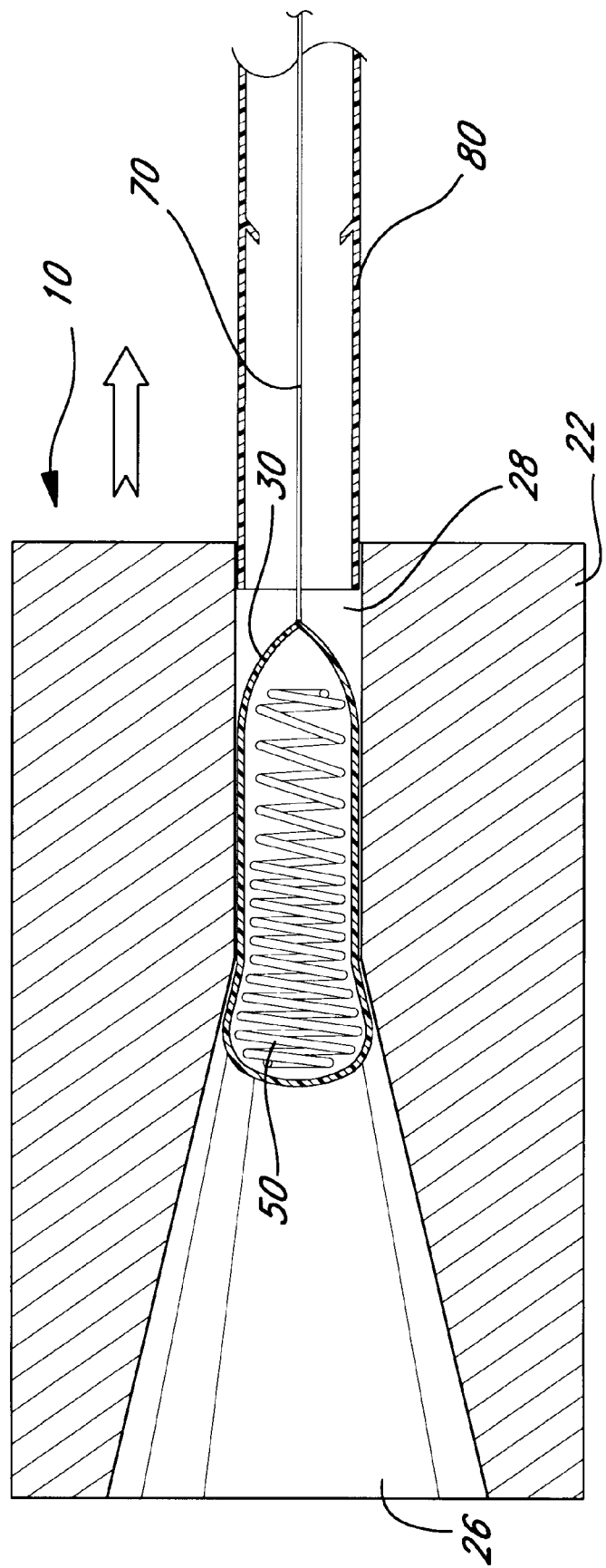
FIG. 6 is a longitudinal-sectional view of an additional embodiment of the stent loading apparatus wherein the bag is pulled through the catheter.

FIG. 6 shows an alternate embodiment where the sleeve 30 is pulled through the catheter. In this embodiment the sleeve 30 can be closed at both ends. A pull string 70 is attached to the proximal end of the sleeve 30 and threaded through the catheter. The string is then used to pull the stent 50 into the end of the catheter 80. If the sleeve 30 is equipped with perforations, the pull string 70 can be used to remove the sleeve 30 from the stent either before or after the catheter 80 is inserted into a patient.

FIG. 7 shows the embodiment of FIG. 1 being used with an open-ended sleeve. All of the embodiments of the current invention can be used with either close or open ended sheaths. The stent or the inner surface of the sleeve are advantageously coated with a material like rosin to prevent or control slippage of the sleeve relative to the stent.

Having thus describe a preferred embodiment of a sleeved stent loading apparatus, it will be apparent by those skilled in the art how certain advantages of the present invention have been achieved. It should also be appreciated that various modifications, adaptations, and alternative embodiments thereof may be made within the scope and spirit of the present invention. The described embodiments are to be considered illustrative rather than restrictive. The invention is further defined by the following claims.

I claim:

1. An apparatus for loading a catheter assembly comprising:
    a flexible sleeve that envelopes a stent placed within;
    a loading device comprising a passageway, wherein said passageway tapers from a larger first diameter to a smaller second diameter; and
    means for pulling the flexible sleeve through the passageway so that the sleeve and the stent enveloped therein are compressed by the passageway tapering from the first diameter to the second diameter.

2. The apparatus described in claim 1, wherein said sleeve further includes a tear strip for opening the sleeve.

3. The apparatus described in claim 1, wherein said sleeve further includes seams or perforations for opening the sleeve.

4. The apparatus described in claim 1, wherein said sleeve further comprises a coated interior to hold said stent in position and a coated exterior to minimize friction.

5. The apparatus described in claim 1, wherein a cross-section of said second diameter is circular.

6. The apparatus described in claim 1, wherein a cross-section of said second diameter shows a plurality of rounded lobes.

7. The apparatus described in claim 6, wherein spacing of the lobes is selected to induce folding during compression of the stent.

8. The apparatus described in claim 1, wherein said device further comprises an intermediate diameter at a distal end of said passageway which is larger than said second diameter but smaller than said first diameter, and wherein said intermediate diameter is sized to accommodate a catheter into which a stent is to be loaded.

9. A method for loading a stent onto or into a catheter comprising:
    providing a loading device comprising a passageway, wherein said passageway tapers from a larger first diameter to a smaller second diameter;
    making a sleeved stent by placing a flexible sleeve over said stent;
    placing said sleeved stent into said loading device in said tapered portion of said passageway so that an end of the sleeve can be grasped from a smaller diameter end of the passageway;
    placing said catheter at or into the smaller diameter end of the passageway; and
    pulling said sleeve through the smaller diameter end of the passageway so that said stent is reduced in diameter and moved onto or into said catheter.

10. The method described in claim 9, wherein said sleeve has a closed-end.

11. An apparatus for loading a catheter assembly comprising:
    a flexible sleeve having a closed end enveloping a stent placed within;
    a loading device comprising a passageway, wherein said passageway tapers from a larger first diameter to a smaller second diameter; and
    means for pulling the flexible sleeve through the passageway so that the sleeve and the stent enveloped therein are compressed by the passageway tapering from the first diameter to the second diameter.

12. An apparatus for loading a catheter assembly comprising:
    a flexible sleeve that envelopes a stent placed within, wherein said sleeve further includes a tear strip for opening the sleeve;
    a loading device comprising a passageway, wherein said passageway tapers from a larger first diameter to a smaller second diameter; and means for pulling the flexible sleeve through the passageway so that the sleeve and the stent enveloped therein are compressed by the passageway tapering from the first diameter to the second diameter.

13. An apparatus for loading a catheter assembly comprising:
   a flexible sleeve that envelopes a stent placed within;
   a loading device comprising a passageway, wherein said passageway tapers from a larger first diameter to a smaller second diameter; and
   means for pulling the flexible sleeve through the passageway so that the sleeve and the stent enveloped therein are compressed by the passageway tapering from the first diameter to the second diameter, wherein a cross-section of said second diameter shows a plurality of rounded lobes.

14. An apparatus for loading a catheter assembly comprising:
   a flexible sleeve that envelopes a stent placed within;
   a loading device comprising a passageway, wherein said passageway tapers from a larger first diameter to a smaller second diameter; and
   means for pulling the flexible sleeve through the passageway so that the sleeve and the stent enveloped therein are compressed by the passageway tapering from the first diameter to the second diameter, wherein a cross-section of said second diameter shows a plurality of rounded lobes, wherein spacing of the lobes is selected to induce folding during compression of the stent.

15. A method for loading a stent onto or into a catheter comprising.
   providing a loading device comprising a passageway, wherein said passageway tapers from a larger first diameter to a smaller second diameter;
   making a sleeved stent by placing a flexible sleeve with a closed end over said stent;
   placing said sleeved stent into said loading device in said tapered portion of said passageway so that an end of the sleeve can be grasped from a smaller diameter end of the passageway;
   placing said catheter at or into the smaller diameter end of the passageway; and
   pulling said sleeve through the smaller diameter end of the passageway so that said stent is reduced in diameter and moved onto or into said catheter.

* * * * *